US005760262A

United States Patent [19]

DeSoto et al.

[11] Patent Number: 5,760,262
[45] Date of Patent: Jun. 2, 1998

[54] ENHANCED PRODUCTION OF BRIDGED HAFNOCENES

[75] Inventors: Troy E. DeSoto; Ronny W. Lin; John F. Balhoff, all of Baton Rouge, La.

[73] Assignee: Albemarle Corporation, Richmond, Va.

[21] Appl. No.: 877,227

[22] Filed: Jun. 17, 1997

Related U.S. Application Data

[63] Continuation of Ser. No. 718,080, Sep. 17, 1996, abandoned.

[51] Int. Cl.$^6$ ............................................. C07F 7/08
[52] U.S. Cl. ................................................... 556/11
[58] Field of Search ........................................ 556/11

[56] References Cited

U.S. PATENT DOCUMENTS

| | | | |
|---|---|---|---|
| 4,528,408 | 7/1985 | Plummer | 568/808 |
| 4,794,096 | 12/1988 | Ewen | 502/117 |
| 4,892,851 | 1/1990 | Ewen et al. | 502/104 |
| 4,931,417 | 6/1990 | Miya et al. | 502/117 |
| 5,017,714 | 5/1991 | Welborn, Jr. | 556/12 |
| 5,036,034 | 7/1991 | Ewen | 502/117 |
| 5,120,867 | 6/1992 | Welborn, Jr. | 556/12 |
| 5,145,819 | 9/1992 | Winter et al. | 502/117 |
| 5,296,434 | 3/1994 | Karl et al. | 502/117 |
| 5,314,973 | 5/1994 | Welborn, Jr. | 526/126 |
| 5,324,800 | 6/1994 | Welborn, Jr. et al. | 526/160 |
| 5,329,033 | 7/1994 | Spaleck et al. | 556/53 |
| 5,441,920 | 8/1995 | Welborn, Jr. | 502/103 |
| 5,455,365 | 10/1995 | Winter et al. | 556/7 |
| 5,455,366 | 10/1995 | Rohrmann et al. | 556/8 |
| 5,512,693 | 4/1996 | Rosen et al. | 556/7 |
| 5,532,396 | 7/1996 | Winter et al. | 556/11 |
| 5,541,350 | 7/1996 | Murata et al. | 556/10 |
| 5,556,997 | 9/1996 | Strickler et al. | 556/11 |
| 5,569,746 | 10/1996 | Lee et al. | 534/11 |
| 5,585,508 | 12/1996 | Kuber et al. | 556/11 |

FOREIGN PATENT DOCUMENTS

| | | |
|---|---|---|
| 2055218 | 5/1992 | Canada . |
| 2084016 | 5/1993 | Canada . |
| 0530908 | 3/1993 | European Pat. Off. . |
| 0581754 | 2/1994 | European Pat. Off. . |
| 4434640 | 2/1996 | Germany . |
| 646438 | 11/1984 | Switzerland . |

OTHER PUBLICATIONS

Ray and Westland; "The Infrared Spectra of Some Compounds of Zirconium (IV) and Hafnium (IV) Tetrahalides and Ligands Containing Group V Donor Atoms"; Inorganic Chemistry, vol. 4, No. 10, Oct. 1965, pp. 1501–1504.

Spaleck, et al., The Influence of Aromatic Substituents on the Polymerization Behavior of Bridged Zirconocene Catalysts; Organometallics, vol. 13, No. 3, 1994, pp. 954–963.
Spaleck, et al., "High Molecular Weight Polypropylene through Specifically Designed Zirconocene Catalyst"; Angew Chem. Int. Ed. Engl. 1992, vol. 31, No. 10, pp. 1347–1350.
Jordan, et al., "Synthesis and Structures of Neutral and Catonic rac–(Ethylenebis(tetrahydroindenyl)) zirconium (IV) Benzyl Complexes": Organometallics, vol. 9, No. 5, 1990, pp. 1539–1545.
Samuel et al; "η–Cyclopentadienyl and η–Indenyl Compounds of Titanium, Zirconium, and Hafnium Containing σ–Bonded Organic Substituents": Journal of the American Chemical Society, 1973, 95:19; pp. 6263–6237.
The Metallocene Monitor, Special Feature: Exxon, Hoechst, and BASF All Have Parts of Metallocene–Catalyzed Isotactic PP: pp. 4–10: (undated).
Stehling, et al., "ansa–Zirconocene Polymerization Catalysts with Annelated Ring Ligands–Effects on Catalytic Activity and Polymer Chain Length": Organometallics, 1994, vol. 13, No. 3, pp. 964–970.

Primary Examiner—Paul F. Shaver
Attorney, Agent, or Firm—Philip M. Pippenger

[57] ABSTRACT

The reaction between a hafnium tetrahalide-diamine adduct and a metallated bis(cyclopentadienyl-moiety containing) ligand, offers great promise as a way of producing racemic hafnocenes, but involves a number of complications. Tetrahydrofuran, a commonly-used solvent/diluent for such reactions, when present in substantial portions in the liquid reaction medium containing the reactants and/or reaction product(s) has been found to cause a substantial reduction in yields of chiral hafnocenes. Apparently the presence of a substantial amount of THF causes or at least results in the formation of increased amounts of the undesirable meso isomer, tends to cause or result in tar formation, and results in a product having poor filterability. Thus large amounts of THF if fed to the reactor with the reactant(s) are purged to a suitably low level, replaced by a liquid aromatic hydrocarbon, and then the reaction mixture is heated to a higher reaction temperature. Large amounts of liquid paraffins and free diamine in the reaction mixture during reaction also contribute to tar formation and reduction in yields of chiral hafnocene. Thus the presence of such materials in the reaction mixture is kept to a minimum. These process modifications make it possible to increase yields of the chiral hafnocene, to reduce formation of the meso isomer, and to sharply reduce the amount of tar formation in the synthesis of chiral hafnocenes from diamine adducts of hafnium tetrahalide and metallated bis(cyclopentadienyl-moiety containing) ligands. Moreover, the hafnocene reaction product so formed has significantly improved filterability characteristics.

10 Claims, No Drawings

ENHANCED PRODUCTION OF BRIDGED HAFNOCENES

This application is a continuation of application Ser. No. 08/718,080, filed Sep. 17, 1996, now abandoned.

TECHNICAL FIELD

This invention relates to the production of hafnocenes by a highly efficacious process, which makes possible the formation of the desired racemic hafnocenes in higher yields and with improved filterability characteristics.

BACKGROUND

Chiral metallocenes of Group 4 metals (Ti, Zr, Hf) are useful for the synthesis of polyolefins. The racemic form of these metallocenes provides stereoregular poly(alpha-olefins). In addition, the racemic form of these metallocenes are considerably more active as catalysts than the meso form, which produces only atactic polymers. Chiral metallocenes and their use as catalysts in forming isotactic olefin polymers are described, for example, in U.S. Pat. Nos. 4,794,096; 5,017,714; 5,036,035; 5,036,034; 5,145,819; 5,296,434; 5,324,800; 5,329,033; and 5,455,366, the full disclosures of which are incorporated herein by reference.

It has been found that the synthesis of hafnocenes is in general different from the synthesis of zirconocenes and titanocenes. Thus while process technology analogous to that found successful for the synthesis of zirconocenes does produce hafnocenes, the yields of hafnocenes have been relatively low (e.g., in the range of about 25–30%) and filtration of the hafnocene product proved to be difficult. Repeated attempts to improve the hafnocene yields and filterability by process modifications met with failure, either with no improvements or in some cases with further loss in yields and even poorer filterability characteristics. Also the reaction mass tended to comprise mixtures of racemic and meso diastereomers along with other unidentifiable by-products and tars.

THE INVENTION

In view of the situation referred to above, our objective was, if possible, to find a way of producing chiral hafnocenes more efficiently and in higher yields and if also possible, to produce hafnocenes having better filterability characteristics. This invention is deemed to have fulfilled this objective.

The reaction between a hafnium tetrahalide-diamine adduct and a metallated bis(cyclopentadienyl-moiety containing) ligand, while offering great promise as a way of producing racemic hafnocenes, has been found to involve a number of complications. We have found for example that, surprisingly, tetrahydrofuran when present in substantial portions in the liquid reaction medium containing a hafnium tetrahalide or hafnium tetrahalide-diamine adduct and a metallated bis(cyclopentadienyl-moiety containing) ligand and/or the product(s) formed by the co-reaction thereof tends to cause a substantial reduction in yields of chiral hafnocenes. While the reason for this unusual behavior is not completely understood, it appears that the presence of substantial amounts of tetrahydrofuran causes or at least results in the formation of increased amounts of the undesirable meso isomer of the hafnocene such that the product formed contains a mixture of the racemic and meso isomers. Also the presence of a substantial amount of tetrahydrofuran in the system tends to cause or result in tar formation, which of course is most undesirable. On the other hand, use of tetrahydrofuran with metallated cyclopentadienyl ligands is commonplace and in many other respects, desirable. For example, handling metallated cyclopentadienyl ligands such as dilithium [1,1'-dimethylsilanylenebis(indenide)] when in the form of solids can be hazardous as such materials tend to be either pyrophoric or at least very flammable.

It has also been found that temperature regulation and control during the chiral hafnocene synthesis operation can provide significant improvements in the yields of the desired racemic product, in some cases in very unexpected ways.

Thus this invention has made it possible to increase yields of the chiral hafnocene, to reduce formation of the meso isomer, and to sharply reduce the amount of tar formation in the synthesis of chiral hafnocenes from diamine adducts of hafnium tetrahalide and metallated bis(cyclopentadienyl-moiety containing) ligands. Moreover, the hafnocene reaction product formed in the process has significantly improved filterability characteristics.

In accordance with this invention, chiral hafnocene is produced by a process which comprises: (a) feeding to a reactor concurrently or in any sequence (i) a metallated bis(cyclopentadienyl-moiety-containing) ligand in the form of solid particles or in the form of a solution or suspension or slurry in a substantially anhydrous organic liquid solvent or diluent therefor where the ligand is present therein in whatever chemical form or forms such ligand exists when in such solution or suspension or slurry; (ii) a chelate diamine adduct of a hafnium tetrahalide in the form of solid particles or in the form of a solution or suspension or slurry in a substantially anhydrous organic liquid solvent or diluent therefor where the adduct is present therein in whatever chemical form or forms such adduct exists when in such solution or suspension or slurry; and (iii) optionally a separate substantially anhydrous organic liquid solvent or diluent; such that the reactor contains a continuous liquid phase with solid particles therein; and (b) maintaining the temperature of the liquid phase at one or more reaction temperatures of at least about 10° C. and agitating the contents of the reactor for a sufficient period of time such that a slurry comprising chiral hafnocene of enhanced filterability is produced; all with the proviso that if (1) one or both of feeds (i) and (ii) includes tetrahydrofuran or other cyclic ether in an amount that would cause substantial isomerization and/or by-product formation to occur in the reactor, and/or (2) feed (iii) includes, or is, tetrahydrofuran or other cyclic ether in an amount that would cause substantial isomerization and/or by-product formation to occur in the reactor, the temperature of the liquid phase in the reactor is kept at a low enough temperature during the feeds so that excessive isomerization and/or by-product formation does not occur; and before conducting b), the tetrahydrofuran and/or said other cyclic ether is stripped from the reactor under vacuum at a temperature no higher than about 30° C. to reduce the amount of the tetrahydrofuran and/or said other cyclic ether to below the amount that would cause substantial isomerization and/or by-product formation to occur.

For ease of reference the metallated bis(cyclopentadienyl-moiety-containing) ligand is sometimes hereinafter referred to simply as the ligand. Likewise, the chelate diamine adduct of a hafnium tetrahalide is sometimes hereinafter referred to simply as the adduct.

As those skilled in the art can readily understand and appreciate, the above operations should be conducted in a substantially anhydrous environment and under an inert atmosphere such as dry nitrogen, or other dry inert gases such as argon, neon, krypton, etc.

Still another feature of this invention is the discovery that the presence of substantial amounts of paraffinic hydrocarbons in the reaction mixture during the reaction (e.g., 25 wt % hexane in toluene) can be deleterious as such hydrocarbons tend during the reaction to promote formation of tars, make filtration of the reaction product more difficult and reduce the yield of the desired chiral hafnocene.

These and other features and embodiments of the invention will be still further apparent from the ensuing description and appended claims.

Chiral hafnocenes, such as are produced in accordance with this invention are mixtures of racemic diasteriomers which have no plane of symmetry. The meso isomers, the formation of which is suppressed by this invention, have a plane of symmetry running through the hafnium atom between the rings, and thus are achiral compounds. A few examples of racemic hafnocenes producible pursuant to this invention include:

[1,1'-dimethylsilanylenebis(methylcyclopentadienyl)] hafnium dichloride;

[1,1'-dimethylsilanylenebis(indenyl)]hafnium dichloride;

[1,1'-dimethylsilanylenebis(4,5,6,7-tetrahydroindenyl)] hafnium dichloride;

[1,1'-(1,1,2,2-tetramethyldisilanylene)bis (methylcyclopentadienyl)]hafnium dichloride;

[1,1'-(1,1,2,2-tetramethyldisilanylene)bis(4,5,6,7-tetrahydroindenyl)]hafnium dichloride;

[1,1'-dimethylsilanylenebis (trimethylsilanylcyclopentadienyl)]hafnium dichloride;

[1,1'-(1,1,2,2-tetramethyldisilanylene)bis (trimethylsilanylcyclopentadienyl)]hafnium dichloride;

[1,1'-(1,1,3,3-tetramethyldisilanylene)bis(4,5,6,7-tetrahydroindenyl)]hafnium dichloride;

[1,1'-(1,1,4,4-tetramethyl-1,4-disilanylbutylene)bis(4,5,6,7-tetrahydroindenyl)]hafnium dichloride;

[1,1'-(2,2-dimethyl-2-silapropylene)bis (methylcyclopentadienyl)]hafnium dichloride;

[1,2-ethylenebis(ethylcyclopentadienyl)]hafnium dichloride; and

[1,2-ethylenebis(indenyl)]hafnium dichloride.

The ligand used in the process of this invention, when in isolated and pure form, is preferably a compound of the formula $$Q(Cp^1-M)(Cp^2-M)$$

in which $Cp^1$ and $Cp^2$ independently are cyclopentadienyl-moiety-containing groups having a ring substituent, M, where M is an alkali metal atom or a monohalomagnesium group; and in which Q represents a bridging group that links the Cp groups. The cyclopentadienyl-moiety-containing group before metallation is a cyclopentadienyl, indenyl, fluorenyl, or related group that can $\pi$-bond to a hafnium atom, or a hydrocarbyl (e.g., alkyl, cycloalkyl, aryl, aralkyl, alkenyl, etc.), silanyl, or hydrocarbylmetalloid substituted derivative thereof. Either or both Cp groups can have one or more hydrocarbyl ring system fused thereon. Each Cp may contain up to about 75 nonhydrogen atoms. Q may be any bridging group that is used to link the Cp groups, including, for example, silanylene (—SiR$_2$—), silaalkylene, oxasilanylene, oxasilaalkylene, benzo (C$_6$H$_4$ <) or substituted benzo, methylene (—CH$_2$—) or substituted methylene, ethylene (—CH$_2$CH$_2$—), or substituted ethylene bridges. Methylene and ethylene bridges are preferred, and ligands having silanylene bridges such as dimethylsilanylene, diethylsilanylene, ethylmethylsilanylene, dipropyl-silanylene, and dibutylsilanylene are more preferred.

In forming the ligand, metallation is accomplished in known manner by deprotonating the unmetallated bridged bis(cyclopentadienyl-moiety-containing) compound with a suitable metallating agent such as an alkali metal, an alkali metal hydride, or a Grignard reagent. Examples of deprotonating agents include sodium dispersions, lithium hydride, sodium hydride, potassium hydride, Grignard reagents and organoalkali metal compounds, RM, where R is a $C_1$ to $C_{10}$ hydrocarbyl group (alkyl, aryl, cycloalkyl, etc.) and M is an alkali metal. Preferred are lithium alkyls such as methyllithium, ethyllithium and butyllithium. Metallation is typically accomplished in a suitable anhydrous inert reaction medium such as a dry liquid hydrocarbon.

The adduct is formed from a hafnium tetrahalide in which the halogen atoms have an atomic number of 17 or above (i.e., atoms of chlorine, bromine and/or iodide) and a diamine capable of chelating or complexing therewith to form the adduct. Examples of such diamines include N,N, N',N'-tetramethyl-1,2-ethanediamine, N,N,N',N'-tetramethyl-1,2-propanediamine, N,N,N',N'-tetramethyl-2,3-butanediamine, and N,N,N',N'-tetramethylmethanediamine. Most preferred are the adducts formed from hafnium tetrachloride, especially the adducts of hafnium tetrachloride with N,N,N',N'-tetramethyl-1,2-ethanediamine and with N,N,N',N'-tetramethylmethanediamine.

The ligand and the adduct can be charged to the reactor in the form of solid particles or in the form of solutions or suspensions or slurries in a substantially anhydrous organic liquid solvent or diluent therefor. When charged in neat particulate form, a separate charge of anhydrous liquid organic solvent or diluent is used so that the reaction mixture has a continuous liquid phase in which some of the reactant (s) may dissolve and in which undissolved particles of one or both reactants are suspended or slurried. If the liquid used can dissolve all of the ligand and all of the adduct this would be desirable, but to date no such solvent has been found. Suitable solvents or diluents include inert liquid hydrocarbons, liquid silicones, liquid perfluorocarbons, liquid monoethers, liquid polyethers, and mixtures thereof.

As chemists well know, when the chelate or adduct is in solution or in suspension or slurry it may, in whole or in part, change in chemical form, such as by being solvated, complexed, diassociated or otherwise transformed so that at that time it is not completely identical in chemical structure to the way it was just prior to being placed in the form of a solution, suspension and/or slurry. If any such changes occur when forming such solutions, suspensions and/or slurries, they are within the ambit of this invention as long as ordinary skill of a chemist and common sense were used in selecting the liquid medium in which to form the solution, suspension and/or slurry.

The molar ratio of the diamine-hafnium tetrahalide adduct to the bridged ligand charged to the reactor is typically in the range of about 0.7 to about 1.3 mols (preferably 0.8 to about 1.2, more preferably about 0.9 to about 1.1 mols) of adduct per mol of ligand. A particularly preferred molar ratio is in the range of about 1.00 to about 1.05 mols of adduct per mol of ligand, as this is the most cost-effective range and simplifies work-up and purification procedures when isolating pure racemic product for use as a catalyst ingredient.

As noted above, the adduct and the ligand are fed to the reactor either as solids or as solutions or slurries. Preferably at least the ligand is charged as a solution or slurry in a suitable liquid medium, most preferably in one or more liquid aromatic hydrocarbons, or in a mixture of one or more liquid aromatic hydrocarbons with one or more liquid cyclic or acyclic ethers, or in one or more liquid cyclic or acyclic ethers. When tetrahydrofuran is selected for use care should be taken to keep its concentration in the reaction slurry relatively low (e.g., 15 wt % and preferably even lower. Thus in general, the lower the amount of THF, the better. Indeed, it is most preferred to keep the reaction mixture free of tetrahydrofuran except for trace amounts that may be carried over by one or both of the reactants. It is not known whether other cyclic ethers such as alkyltetrahydrofurans, 1,4-dioxane, tetrahydropyran, etc. will cause problems similar to those experienced when tetrahydrofuran is used. Thus a few pilot experiments should be conducted if such other cyclic ether is selected for use to ensure that at the concentrations, temperatures and reaction times contemplated the cyclic ether will not unduly interfere with the desired reaction or unduly complicate the recovery operations such as filtration.

During a substantial portion of the reaction period the temperature of the reaction mixture is typically maintained in the range of about 25° to about 60° C. A preferred range is about 30° to about 50° C., and the range of about 35° to about 40° C. is particularly preferred as this tends to produce the highest yields of the chiral hafnocene.

As noted above, large amounts of liquid paraffins and of free diamine in the reaction mixture during reaction also contribute to tar formation and reduction in yields of chiral hafnocene. Thus the presence of such materials in the reaction mixture should be kept to a minimum. Thus paraffin hydrocarbon content, if any, of the liquid reaction solvent or diluent during the reaction itself should be kept below about 5% of the total weight of solvent/diluent.

COMPARATIVE EXAMPLE A

Reactions were performed in which hafnium tetrachloride or hafnium tetrachloride di(tetrahydrofuranate) complex was added to a slurry of dilithium [1,1'-dimethylsilanylenebis(indenide)] mono(diethyletherate) in toluene and diethylether under dry nitrogen to provide a slurry containing approximately equimolar amounts of the reactants. The resultant slurry was stirred at about 25° C. for periods in the range of 12–16 hours. Yields of racemic [1,1'-dimethylsilanylenebis(indenyl)]hafnium dichloride were in the range of 25 to 30% based on the dilithium [1,1'-dimethylsilanylenebis(indenide)] etherate charged to the reactor. Filtration of the reaction products was slow, tedious and difficult.

COMPARATIVE EXAMPLE B

An equimolar orange slurry of dilithium [1,1'-dimethylsilanylenebis(indenide)] mono- (diethyletherate) and hafnium tetrachloride in toluene was stirred overnight at room temperature. Filtration of the reaction mixture yielded a pale yellow solid and an orange filtrate. Extraction of the solids into methylene dichloride gave an isolated yield of 30% of pure racemic [1,1'-dimethylsilanylenebis(indenyl)] hafnium dichloride. It required over one hour to filter about 30 to 40 mL of the reaction slurry. Examination of the filtrate by ¹H NMR showed the presence of a mixture of racemic and meso diastereomers along with other unidentifiable by-products and oligomers.

COMPARATIVE EXAMPLE C

The procedure of Comparative Example B was repeated except that an equal volume of tetrahydrofuran was added to the reaction slurry at the end of the reaction time in hopes of improving the situation. This addition resulted in the disappearance of most of the solids and formation of a dark orange solution. Examination of the filtrate by ¹H NMR showed the presence of a mixture of racemic and meso isomers.

COMPARATIVE EXAMPLE D

The procedure of Comparative Example B was again repeated except that the reactants in the form of dry solids were mixed together at −78° C., and toluene at −78 °C. was added to form the reaction slurry. Work-up gave the same result as in Comparative Example B.

COMPARATIVE EXAMPLE E

Another attempt was made to improve the procedure of Comparative Example B by conducting the reaction in the same manner with the exception that the orange reaction mixture was refluxed for about 16 hours. Work-up gave essentially the same result but with even less racemic [1,1'-dimethylsilanylenebis(indenyl)]hafnium dichloride produced.

COMPARATIVE EXAMPLE F

Dilithium [1,1'-dimethylsilanylenebis(indenide)] mono (diethyletherate) was dissolved in tetrahydrofuran and then stripped to dryness affording a sticky residue. An equimolar amount of hafnium tetrachloride and toluene diluent were added to this residue and the reaction was conducted as in Comparative Example B. In this case the yield of racemic [1,1'-dimethylsilanylenebis (indenyl)]hafnium dichloride was only 15%.

COMPARATIVE EXAMPLE G

A 31 wt % solution of dilithium [1,1'-dimethylsilanylenebis(indenide)] mono(diethyletherate) in tetrahydrofuran was added to a hafnium tetrachloride-N,N, N',N'-tetramethylethanediamine (TMEDA) adduct (HfCl$_4$·TMEDA) in toluene at about −5° C. The reactants were charged in approximately equimolar amounts. A very dark wine red solution was produced from which only a dark oily material could be isolated.

EXAMPLE 1

The procedure of Comparative Example G is repeated except that instead of adding the ligand to the adduct at about −5° C., the addition of the concentrated (31%) ligand-THF solution was added to the adduct-toluene slurry at ambient room temperature (ca. 25° C.). In a reaction conducted in this manner, surprisingly, the reaction mixture was a much lighter colored slurry, indicating that THF can be tolerated if the amount of THF in the reaction mixture is not excessive and if the reactants are caused to promptly commence reacting at a temperature sufficiently above −5° C. for a suitably short reaction period.

EXAMPLE 2

The procedure of Example 1 is repeated except that the tetrahydrofuran is stripped off from the initial reaction mixture slurry in the reactor as soon as possible and if necessary, replaced by a similar amount of toluene or other liquid aromatic hydrocarbon diluent. The reaction period can then be as long as needed to achieve the desired yield of product. The stripping is conducted at reduced pressure, and thus distillation equipment is unnecessary for this operation. In a reaction conducted in this general manner on a relatively large scale (21 g of HfCl$_4$ was used), the THF was successfully removed 1.3 hours after the feed of the concentrated ligand-THF solution to the adduct-toluene slurry by stripping at 23 mm Hg at 20° C. A yield of 66% of racemic [1,1'-dimethylsilanylenebis(indenyl)]hafnium dichloride was achieved.

EXAMPLE 3

Hafnium tetrachloride (3.2 g; 10 mmol) and N,N,N',N'-tetramethylethanediamine (TMEDA) (1.2 g; 10.3 mmol) in 10 g of toluene are stirred at 90° C. for 1 hour to produce the HfCl$_4$·TMEDA adduct. After cooling the adduct-toluene mixture to below 25° C., dilithium [1,1'-dimethylsilanylenebis(indenide)] mono(diethyletherate) 3.74 g; 9.72 mmol; 97.2% purity by NMR) and 5 g of toluene are added with stirring. During the addition the temperature of the stirred mixture increases to about 28° C. by virtue of heat of reaction. The slurry is then heated up to 35°–40° C. and stirred at about 35° C. for 22 hours. The reaction mixture is then slowly cooled down to room temperature, and is more readily filtered. The filter cake is washed with about 4 g of fresh toluene. In an operation conducted in this general manner 4.38 g of dried crude filter cake (which contained lithium chloride) was recovered. Examination of this product by NMR with internal standard indicated that it contained 73.7 wt % of pure racemic (1,1'-dimethylsilanylenebis(indenyl))hafnium dichloride. Thus the yield was 61.8% based on the dilithium [1,1'-dimethylsilanylenebis(indenide)]etherate. The filtration step was conducted without difficulty.

EXAMPLE 4

Example 3 is repeated in the same manner except that the reaction mixture is stirred at ambient room temperature for 72 hours. In an operation conducted in this general manner, the yield as determined by NMR with internal standard was 60.4% based on the dilithium [1,1'-dimethylsilanylenebis(indenide)]etherate added to the reactor. The filtration was not difficult, but was slower than in Example 1.

EXAMPLE 5

The same general procedure of Example 3 is used except that the reaction mixture is stirred at ambient room temperature (ca. 25° C.) for 22 hours. In a run conducted in this manner filtration, although still slower, was not particularly difficult. NMR (without internal standard) indicated a normalized expected yield of about 54%. NMR with internal standard indicated a 35% yield.

EXAMPLE 6

To a 100 mL flask equipped with a magnetic stirring bar are charged HfCl$_4$ (6.22 g; 19.4 mmol) and 17 g of toluene. The slurry is treated with 2.36 g of TMEDA at ambient temperature and then heated to 80°–90° C. for 45 minutes, and then allowed to stir at room temperature for 4 days. The resulting HfCl$_4$·TMEDA adduct in toluene is kept available for use in the ensuing reaction with the ligand. A solution of dilithium [1,1'-dimethylsilanylenebis(indenide)] mono (diethyletherate) (23.55 g of 31 wt % solution in THF) is charged to another flask containing a stir bar. To this is added 26.5 g of toluene. This mixture is stirred while removing solvents (29.5 g of a 1:2 mixture of THF and toluene) in a vacuum. To the stripped mixture is added 6.0 g of fresh toluene to form a cloudy ligand mixture which is added to the foregoing HfCl$_4$·TMEDA adduct-toluene mixture over a two-minute period. An additional 4 g of toluene is used to wash the ligand mixture into the adduct-toluene mixture. After stirring a few more minutes, 6 g of solvents (1:2 mixture of THF and toluene) are removed under vacuum. The reaction mixture is then stirred for 16 hours at 30°–35° C. then allowed to cool to room temperature for 3 hours. In an operation conducted in this general manner, a sample of the liquid phase of the final product was found to contain 8.5% THF with the remainder being toluene. The reaction product mixture was suction filtered through a medium-porosity glass frit. The filtration was very rapid. The solids were washed with toluene and dried by pulling a vacuum on the frit. The dried weight of the crude product was 8.2 g containing 74% racemic [1,1'- dimethylsilanylenebis (indenyl)]hafnium dichloride. A 58% yield of racemic [1,1'-dimethylsilanylenebis(indenyl)]dichloride was thus achieved.

EXAMPLE 7

Under a nitrogen pad, 3.60 g of TMEDA (30.9 mmol) is added into 9.60 g of HfCl$_4$ mmol) slurried in toluene (30 g) at ambient room temperature. With good mixing, the slurry is heated up (from ca. 35° C.) to and stirred at ca. 90° C. for 1 hour. Then 11.22 g of dilithium [1,1'-dimethylsilanylenebis(indenide)]mono(diethyletherate) solid (ca. 97%; 29.1 mmol) and 15 g of toluene are then added into the HfCl$_4$·TMEDA adduct slurry at about ambient room temperature in a nitrogen atmosphere. The resultant slurry is heated up to and kept at about 36°–38° C. for ca. 22 hours. After being slowly cooled down, the slurry is filtered in a dry box. The wet cake is washed with 9 g of toluene and dried to obtain a product which typically has ca. 77 wt % racemic [1,1'-dimethylsilanylenebis(indenyl)] hafnium dichloride and no detectible meso isomer by NMR with internal standard. The isolated yield in a run conducted in this manner was 74.2%.

EXAMPLE 8

Add 6.41 g of HfCl$_4$ (20 mmol) to 38.7 g of toluene. While stirring the HfCl$_4$ slurry at ambient room temperature, add 2.46 g of TMEDA (21.2 mmol) in a period of 10–15 minutes. Heat the slurry to ca. 80° C. for 1 hour and then cool to −5° C. Add to the slurry over a 15minute period, 23.96 g (19.85 mmol) of dilithium [1,1'-dimethylsilanylenebis(indenide)]mono-(diethyletherate) as a 31 wt % solution in tetrahydrofuran. Apply a vacuum and allow the reaction mixture to warm up. Strip off ca. 85% of the solvent from 11° C. to 18° C. Heat the reaction mixture to 30°–35° C. while adding 6.4 g of toluene. Stir the reaction mixture for 16 hours and then filter it at ambient room temperature. Wash the filter cake with 20 g of toluene and 5.4 g of diethyl ether. The dried product contains ca. 80 wt % of racemic [1,1'-dimethylsilanylenebis(indenyl)]hafnium-dichloride and less than 1 wt % HfCl$_4$·TMEDA adduct. The yield in a run conducted in this manner was about 65 %.

The materials referred to by chemical name or formula anywhere in the specification or claims hereof are identified as ingredients to be brought together in connection with performing a desired operation or in forming a mixture to be used in conducting a desired operation. Accordingly, even though the claims hereinafter may refer to substances in the present tense ("comprises", "is", etc.), the reference is to the substance, as it existed at the time just before it was first contacted, blended or mixed with one or more other substances in accordance with the present disclosure. The fact that a substance may lose its original identity through a chemical reaction, complex formation, salvation, ionization, or other transformation during the course of contacting, blending or mixing operations, if done in accordance with the disclosure hereof a and with the use of ordinary skill of a chemist and common sense, is within the purview and scope of this invention.

Each and every patent or other publication referred to in any portion of this specification is incorporated in toto into this disclosure by reference, as if fully set forth herein.

This invention is susceptible to considerable variation in its practice. Therefore the foregoing description is not intended to limit, and should not be construed as limiting, the invention to the particular exemplifications presented hereinabove. Rather, what is intended to be covered is as set forth in the ensuing claims and the equivalents thereof permitted as a matter of law.

What is claimed is:

1. A process for the production of chiral hafnocene, said process comprising:

a) feeding to a reactor concurrently or in any sequence (i) a metallated bis(cyclopentadienyl) ligand in the form of solid particles or in the form of a solution or suspension or slurry in a substantially anhydrous organic liquid solvent or diluent therefor, wherein the metallated ligand is present therein in whatever chemical form or forms such ligand exists when in such solution or suspension or slurry; (ii) a diamine adduct of a hafnium tetrahalide in the form of solid particles or in the form of a solution or suspension or slurry in a substantially anhydrous organic liquid solvent or diluent therefor, wherein the adduct is present therein in whatever chemical form or forms such adduct exists when in such solution or suspension or slurry; and (iii) optionally a separate substantially anhydrous organic liquid solvent or diluent; such that the reactor contains a continuous liquid phase with solid particles therein; and b) maintaining the temperature of the liquid phase at one or more reaction temperatures of at least about 10° C. and agitating the contents of the reactor for a sufficient period of time such that a slurry comprising chiral hafnocene of enhanced filterability is produced; with the proviso that (1) if one or both of feeds (i) and (ii) includes tetrahydrofuran or other cyclic ether in an amount that would cause substantial isomerization and/ or by-product formation to occur in the reactor; and/or (2) feed (iii) includes, or is, tetrahydrofuran or other cyclic ether in an amount that would cause isomerization and/or by-product formation to occur in the reactor, the temperature of the liquid phase in the reactor is controlled so that excessive isomerization and/or by-product formation does not occur; and before conducting b), the tetrahydrofuran and/or said other cyclic ether is stripped from the reactor under vacuum at a temperature no higher than about 30° C. to reduce the amount of the tetrahydrofuran and/or said other cyclic ether to below the amount that would cause substantial isomerization and/or by-product formation to occur.

2. A process according to claim 1 wherein the slurry is filtered to recover chiral hafnocene therefrom.

3. A process according to claim 1 wherein (i) is fed into (ii).

4. A process according to claim 3 wherein the slurry is filtered to recover chiral hafnocene therefrom.

5. A process according to any of claims 1 to 4 taken individually wherein (ii) is a suspension or slurry of an adduct of N,N,N',N'-tetramethyl-1,2-ethanediamine or N,N, N',N'-tetramethyl-ethanediamine and a hafnium tetrahalide in which the halogen atoms have an atomic number of 17 or above in a substantially anhydrous liquid aromatic hydrocarbon in whatever chemical form or forms such adduct exists when in such suspension or slurry.

6. A process according to any of claims 1 to 4 taken individually wherein said ligand when in isolated and pure form is a compound of the formula

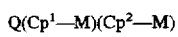

in which $Cp^1$ and $Cp^2$ independently are cyclopentadienyl-moiety-containing groups having a ring substituent, M, where M is an alkali metal atom or a monohalomagnesium group; and in which Q represents a bridging group that links the Cp groups; and wherein said ligand is in the form of solid particles or in the form of a solution or a suspension or slurry in a substantially anhydrous organic liquid solvent or diluent therefor and is present therein in whatever chemical form or forms such ligand exists when in such solution or suspension or slurry.

7. A process according to any of claims 1 to 4 taken individually wherein said ligand when in isolated and pure form is a compound of the formula

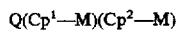

in which $Cp^1$ and $Cp^2$ independently are cyclopentadienyl-moiety-containing groups having a ring substituent, M, where M is a lithium atom; and in which Q represents a 1,1'-dialkylsilanylene group linking the Cp groups; and wherein said ligand is in the form of solid particles or in the form of a solution or a suspension or slurry in a substantially anhydrous organic liquid solvent or diluent therefor and is present therein in whatever chemical form or forms such ligand exists when in such solution or suspension or slurry.

8. A process according to any of claims 1 to 4 taken individually wherein said ligand when in isolated and pure form is a dilithium [1,1'-dimethylsilanylene-bis(indenide)] dihydrocarbyl etherate in which one or both of the indenide rings optionally contain one or more $C_1$-$C_4$ alkyl substituents thereon or have an additional ring system fused thereon; wherein (ii) is a suspension or slurry of an adduct of N,N,N',N'-tetramethyl-1,2-ethanediamine and hafnium tetrachloride in a substantially anhydrous liquid aromatic hydrocarbon in whatever chemical form or forms such adduct exists when in such suspension or slurry; wherein the molar ratio of said adduct to said ligand is about 0.7 to about 1.3 mols of said adduct per mol of said ligand; and wherein during a substantial portion of the reaction period of b) the temperature of the reaction mixture is maintained in the range of about 25° to about 60° C.

9. A process according to claim 1 wherein:

1) (i) is either (A) a suspension or slurry in a substantially anhydrous liquid medium composed substantially entirely of aromatic hydrocarbon of dilithium [1,1'-dimethylsilanylene-bis(indenide)]diethyl etherate ligand in whatever chemical form or forms such ligand exists when in such suspension or slurry, or (B) finely-divided dilithium [1,1'-dimethylsilanylene-bis (indenide)]diethyl etherate optionally fed concurrently or sequentially with (iii) a separate feed of liquid aromatic hydrocarbon;

2) (ii) is a suspension or slurry in a substantially anhydrous liquid medium composed substantially entirely of aromatic hydrocarbon of a finely-divided adduct of N,N,N',N'-tetramethyl-1,2-ethanediamine and hafnium tetrachloride in whatever chemical form or forms such adduct exists when in such suspension or slurry;

3) (i)(A) or (i)(B), as the case may be, is fed into (ii) while maintaining the resultant mixture at or below about 28° C.;

4) the molar ratio of said adduct to said ligand fed to the reactor is about 0.9 to about 1.1 mols of said adduct per mol of said ligand;

5) during a substantial portion of the reaction period of b) the temperature of the reaction mixture is maintained in the range of about 30° to about 40° C.; and 6) the reaction mixture is filtered to recover racemic [1,1'-dimethylsilanylenebis(indenyl)]hafnium dichloride.

10. A process according to claim 1 wherein:

1) (i) is a suspension or slurry in a substantially anhydrous liquid medium composed substantially entirely of aromatic hydrocarbon of dilithium [1,1"-dimethylsilanylenebis(indenide)]diethyl etherate ligand in whatever chemical form or forms such ligand exists when in suspension or slurry;

2) (ii) is a mixture of (A) a substantially anhydrous liquid medium composed substantially entirely of tetrahydrofuran and (B) an adduct of N,N,N',N'-tetramethyl-1,2-ethanediamine and hafnium tetrachloride in whatever chemical form or forms such adduct exists when in such mixture;

3) (ii) is cooled to a temperature in the range of about −5° C. to about 5° C., and while keeping the temperature substantially continuously in said range (i) is added portionwise to (ii), and then a vacuum is applied to the reactor and the resultant mixture is warmed or allowed to warm to about 20° C. to strip off a substantial portion of the tetrahydrofuran;

4) liquid aromatic hydrocarbon is fed to the stripped mixture to replace the tetrahydrofuran stripped therefrom;

5) the molar ratio of said adduct to said ligand fed to the reactor is about 0.9 to about 1.1 mols of said adduct per mol of said ligand;

6) during a substantial portion of the reaction period of b) the temperature of the reaction mixture is maintained in the range of about 30° to about 40° C.; and 7) the reaction mixture is filtered to recover racemic [1,1'-dimethylsilanylenebis(indeyl)]hafnium dichloride.

* * * * *

UNITED STATES PATENT AND TRADEMARK OFFICE
CERTIFICATE OF CORRECTION

PATENT NO. : 5,760,262
DATED : June 2, 1998
INVENTOR(S) : Troy E. DeSoto, Ronny W. Lin, and John F. Balhoff It is certified that error appears in the above-identified patent and that said Letters Patent is hereby corrected as shown below:

Column 10, Line 2, reads "ethanediamine" and should read -- methanediamine --.

Signed and Sealed this

First Day of June, 1999

Attest:

Q. TODD DICKINSON

Attesting Officer

Acting Commissioner of Patents and Trademarks